US00PP15895P2

(12) United States Plant Patent
Olesen et al.

(10) Patent No.: US PP15,895 P2
(45) Date of Patent: Jul. 26, 2005

(54) COMPACT FLORIBUNDA ROSE PLANT NAMED 'POULAC014'

(50) Latin Name: *Rosa hybrida*
Varietal Denomination: Poulac014

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 25 days.

(21) Appl. No.: 10/812,709

(22) Filed: Mar. 29, 2004

(51) Int. Cl.[7] ..... A01H 5/00
(52) U.S. Cl. ..... Plt./141
(58) Field of Search ..... Plt./143, 146, 147, Plt./141

*Primary Examiner*—Anne Marie Grunberg
*Assistant Examiner*—June Hwu

(57) ABSTRACT

A new garden rose plant of the compact floribunda class which has abundant, apricot flowers and attractive foliage. This new and distinct variety has shown to be uniform and stable in the resulting generations from asexual propagation.

1 Drawing Sheet

Botanical classification: *Rosa hybrida.*
Variety denomination: 'Poulac014'.

SUMMARY OF THE INVENTION

The present invention constitutes a new and distinct variety of garden rose plant which originated from a controlled crossing between the female seed parent plant, an un-named seedling, and the male pollen parent plant, an un-named seedling. The two parents were crossed during the summer of 1995 and the resulting seeds were planted in a controlled environment in Fredensborg, Denmark. The new variety is named 'Poulac014'.

The new variety may be distinguished from its unnamed female seed parent, by the following combination of characteristics:

1. While the seed parent has yellow flowers, 'Poulac04' has apricot flowers.
2. While the seed parent has acute flower petal bases, 'Poulac014' has rounded to acute flower petal base shapes.

The new variety may be distinguished from its male pollen parent by the following combination of characteristics:

1. 'Poulac014' has larger leaves than those of the pollen parent.
2. 'Poulac014' has larger flowers than the pollen parent.

The objective of the hybridization of this rose variety was to create a new and distinct variety for garden use with unique qualities, such as:

1. Uniform and abundant apricot flowers;
2. Vigorous, but compact growth when propagated both as a budded rose and on its own roots;
3. Disease resistance.

This combination of qualities is not present in previously available commercial cultivars of this type, known to the inventors, and distinguish 'Poulac014' from all other varieties of which we are aware.

As part of their rose development program, L. Pernille Olesen and Mogens N. Olesen germinated the seeds from the aforementioned hybridization during winter of 1995 and conducted evaluations on the resulting seedlings in a controlled environment in Fredensborg, Denmark.

'Poulac014' was selected in the spring 1996 by the inventors as a single plant from the progeny of the aforementioned hybridization.

Asexual reproduction of 'Poulac014' by traditional budding and rooted cuttings was first done by L. Pernille and Mogens N. Olesen in their nursery in Fredensborg, Denmark in July, 1996. This initial and other subsequent asexual propagations conducted in controlled environments have demonstrated that the characteristics of 'Poulac014' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulac014'. Specifically illustrated in the Sheet 1

FIG. 1.1; Open flowers, above view and side view;

FIG. 1.2; Flower bud closed, flower bud as sepals unfold, and partially open;

FIG. 1.3; Flower petals, detached;

FIG. 1.4; Sepals, receptacle, and peduncle;

FIG. 1.5; Juvenile leaf exhibiting anthocyanin;

FIG. 1.6; Mature Leaf;

FIG. 1.7; Bare stems, exhibiting thorns.

DETAILED DESCRIPTION OF THE VARIETY

The following is a description of 'Poulac014', as observed in its growth in a field nursery in Jackson County, Oreg. Observed plants are 3 years of age. Plants were grown on *Rosa multiflora* understock. Color references are made using The Royal Horticultural Society (London, England) Colour Chart, 1995, except where common terms of color are used.

For a comparison, several physical characteristics of the rose variety 'Poulymp', a rose variety from the same inventors described and illustrated in U.S. Plant patent application Ser. No. 09/607,327 dated Jun. 30, 2000, are compared to 'Poulac014' in Chart 1.

CHART 1

| | 'Poulac014' | 'Poulymp' |
|---|---|---|
| Flower Diameter | 60 to 65 mm | 60 to 70 mm |
| Petalage | 30 to 35 petals | 25 to 30 petals |
| Flower Color after opening: Upper surface of outermost petals. | Orange Group 25B at marginal to middle zone, becoming Yellow-Orange Group 14A at basal zone. | Yellow-Orange Group 21 C |

FLOWER AND FLOWER BUD

Blooming habit: Continuous.

Flower bud:

*Size.*—Upon opening, 28 mm in length from base of receptacle to end of bud. Bud diameter is 17 mm on average.

*Bud form.*—Pointed ovoid with broad base.

*Bud color.*—As sepals unfold, petals are Orange Group 25D to Yellow Group 12C.

*Sepals.*—Upper surface: Color: Yellow-Green Group 144A to 144B. Surface: Moderately pubescent. Lower surface: Color: Yellow-Green Group 144A. Sepal shape: Sepal apex is cirrhose. Base is flat at union with receptacle. Sepal margin: Margins have strong foliaceous appendages on three of the five sepals. Size: 28 mm (l)×8 mm (w).

*Receptacle.*—Surface texture: Smooth to Glabrous. Shape: Funnel shaped. Size: 4 mm (h)×8 mm (w). Color: Yellow-Green Group 144B.

*Pedicel.*—Surface: Smooth. Few to medium quantity of stipitate glands towards base of peduncle. Length: 25 to 30 mm. Diameter: 3 mm on average. Color: Yellow-Green Group 145B Anthocyanic pigments the color of Greyed-Red Group 180C observed. Strength: Strong.

*Borne.*—In clusters of 1 to 4 flower buds per stem.

Flower bloom:

*Fragrance.*—Moderate floral scent.

*Duration.*—The blooms have a duration on the plant of approximately 10 days. Petals fall cleanly away from plant after flowers have matured compleltely.

*Size.*—Flower diameter is 60 to 65 mm when open. Flower depth is 30 to 35 mm.

*Form.*—General shape is a deep cup. Shape of flower when viewed from the side: Upon opening, upper part: Flat. Upon opening, lower part: Flat. Open flower, upper part: Flat. Open flower, lower part: Concave.

Petalage: Average range is 30 to 35 petals under normal conditions with 7 petaloids.

Color:

Upon opening, petals:

*Outermost petals.*—Outer side: Orange-Red Group 34A at marginal zone, blending with Orange-Red Group 34C at the middle zone. Intonations of and Yellow Group 12A to 12B at basal zone. Inner side: Orange Group 25B. Blended intonations of Red Group 34C at margins. Distinctly Yellow Group 14A at basal zone.

*Innermost petals.*—Outer side: Orange-Red Group 34A at marginal zone, blending with Orange-Red Group 34C at the middle zone. Distinctly Yellow Group 12A to 12B at basal zone. Inner side: Orange Group 25B with blended intonations of Red Group 34C at margins. Distinctly Yellow Group 14A at basal zone.

After opening, petals:

*Outermost petals.*—Outer side: Orange-Red Group 34C at marginal to middle zones, becoming Yellow Group 12A to 12B at basal zone. Inner side: Orange Group 25B at marginal to middle zone, becoming Yellow-Orange Group 14A at basal zone.

*Innermost petals.*—Outer side: Orange-Red Group 30A to Orange-Red Group 34B at marginal to middle zones, becoming Yellow-Orange Group 14A at basal zone. Inner side: Orange Group 26A, becoming Yellow-Orange Group 14A at basal zone.

General tonality: On open flower Orange Group 25B with intonations of Orange-Red Group 33B to 33C. No change in the general tonality at the end of the $10^{th}$ day. Afterwards, general tonality is Yellow-Orange Group 23C to 23D.

Petals:

*Petal reflex.*—Outer petals are somewhat reflexed.

*Margin.*—Entire and uniform with an occasional cleft. Medium undulations of margin observed.

*Shape.*—Apex: Round. Base: Round to acute.

*Size.*—35 mm (l)×32 mm (w).

*Texture.*—Smooth.

*Thickness.*—Thick.

*Arrangement.*—Not Formal.

Petaloids:

*Quantity.*—5 to 9.

*Color.*—Upper surface: Yellow-Orange Group 23A to Yellow Group 12A. Lower surface: Orange-Red Group 34C to Yellow Group 12A.

*Size.*—20 mm (l)×10 mm (w).

*Shape.*—Apex is round. Base is rounded to acute.

Reproductive organs:

*Pistils.*—Length: 8 mm. Quantity: 39 (actual count).

*Pollen.*—None observed.

*Anthers.*—Size: 2 mm in length. Color: Yellow Group 10A. Quantity: 84 (actual count).

*Filaments.*—Color: Yellow Group 13A. Length: 10 mm.

*Stigmas.*—Inferior relative to the length of the filaments and the height of the anthers. Color: Greyed-Yellow Group 162D.

*Styles.*—Color: Red-Purple Group 57A. Length: 10 mm on average.

*Hips.*—None Observed in the field nursery in Jackson County Oreg.

PLANT

Plant growth: Compact, upright to bushy. When grown as a budded field grown plant on *Rosa multiflora* understock, the average height of the plant is 60 cm and the average width is 60 cm.

Stems:

*Color.*—Young wood: Yellow-Green Group 144C. Older wood: Green Group 138B.

*Surface texture.*—Young wood: Smooth. Older wood: Smooth.

Thorns:

*Incidence.*—23 thorns per 10 cm of stem.

*Size.*—Average length: 10 mm.

*Mature color.*—Greyed-Yellow Group 162A.

*Juvenile color.*—Yellow-Green Group 144C to Greyed-Red Group 181A and 181B. Some intonations of Greyed-Yellow Group 162A observed.

*Shape.*—Deeply concave.

Plant foliage: Normal number of leaflets on normal leaves in middle of the stem: 5 leaflets.

*Compound leaf size.*—155 mm (l)×110 mm (w).

*Color.*—Mature foliage: Upper surface is: Yellow-Green Group 147A. Lower surface is: Yellow-Green Group 147B. Juvenile foliage: Upper surface is: Yellow-Green Group 144A. Lower surface is: Yellow-Green Group 147C. Anthocyanin: Location: Juvenile foliage. Color: Greyed-Orange Group 165A to Greyed-Orange Greyed-Orange Group 166A.

Plant leaves and leaflets:

*Stipules.*—Size: 23 mm in length. Shape: Linear. Quantity: 2 per compound leaf. Margins: Finely serrated with abundant stipitate glands at margins and lower side. Color: Green Group 143A.

*Petiole.*—Length: 43 mm. Diameter: 1 mm. Above: Color: Yellow-Green Group 144B. Anthocyanin: Greyed-Red Group 181B. Underneath: Observations: Thorns, fragrant stipitate glands and light pubescence.

*Rachis.*—Length: 65 mm. Above: Color: Yellow-Green Group 144B. Underneath: Observations: Thorns, fragrant stipitate glands, and light pubescence.

*Leaflet.*—Size: 65 mm (l)×41 mm (w). Edge: Shallow serrations. Shape: Ovate. Apex is acute to rounded. Base is rounded. Texture: Smooth. Arrangement: Odd pinnate. Venation: Reticulate. Glossiness: Glossy. Thickness: Thick and leathery.

Disease resistance: Above average resistance to mildew, rust, black spot, and *Botrytis* under normal growing conditions in Jackson County, Oreg.

Cold hardiness: The variety 'Poulac014' has been found to be cold tolerant to USDA Cold Hardiness Zone 6.

It is claimed:

1. A new and distinct variety of rose plant of the compact floribunda rose class named 'Poulac014', substantially as herein illustrated and described as a distinct and novel rose variety due to its abundant apricot flowers, disease resistance, and extended period of bloom.

* * * * *

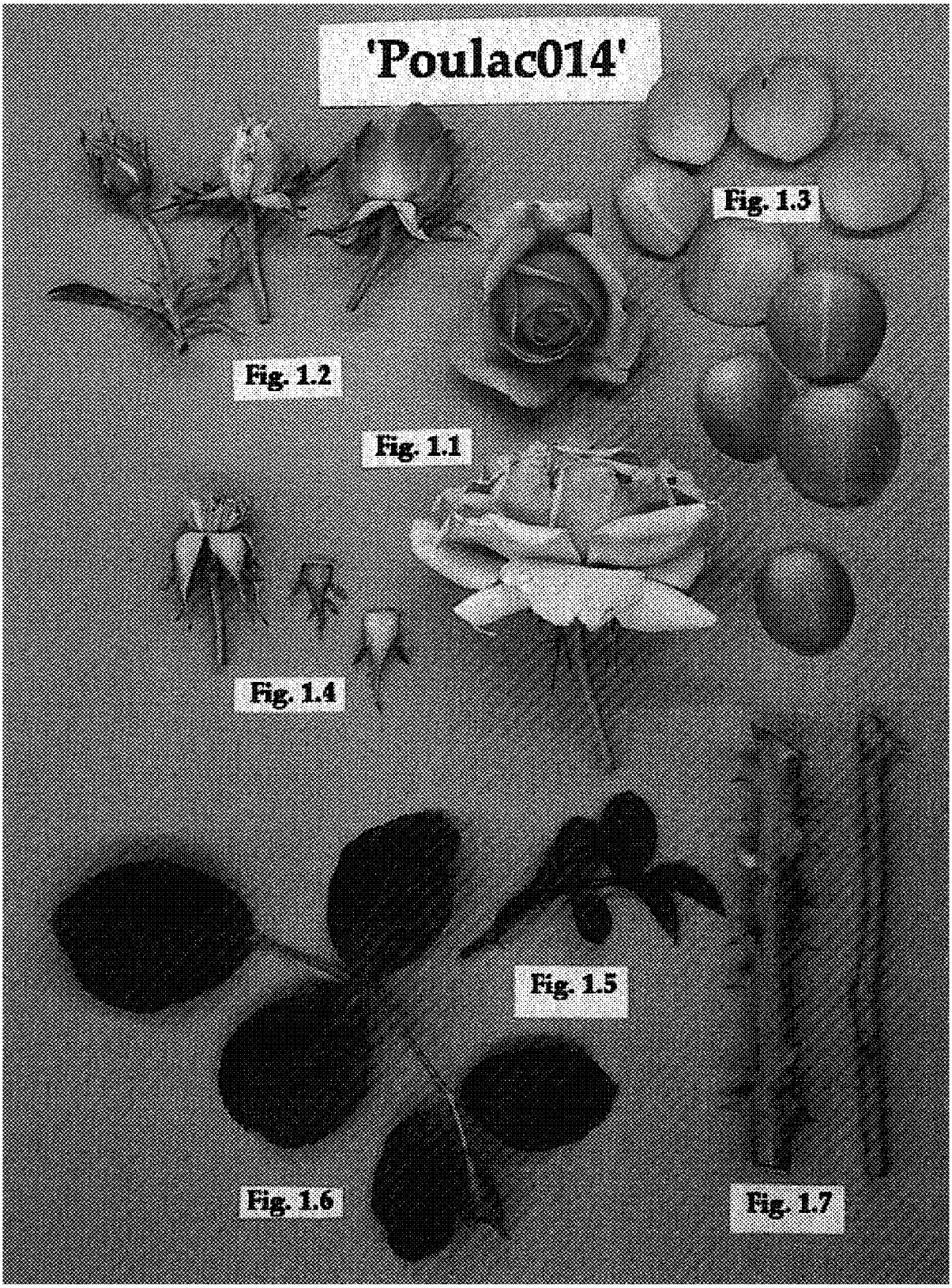
'Poulac014'
Fig. 1.3
Fig. 1.2
Fig. 1.1
Fig. 1.4
Fig. 1.5
Fig. 1.6
Fig. 1.7